US011919967B2

(12) United States Patent
Gonzalez Sarmiento et al.

(10) Patent No.: US 11,919,967 B2
(45) Date of Patent: Mar. 5, 2024

(54) ANTI-PRESENILIN ANTIBODY FOR USE IN THE PREVENTION AND/OR TREATMENT OF CANCER

(71) Applicants: ALZHEIMUR 2012 S.L., Murcia (ES); FUNDACIÓN UNIVERSITARIA SAN ANTONIO, Murcia (ES); IBSAL (INSTITUTO DE INVESTIGACIÓN BIOMEDICA DE SALAMANCA), Salamanca (ES); UNIVERSIDAD DE SALAMANCA, Salamanca (ES)

(72) Inventors: Rogelio Gonzalez Sarmiento, Salamanca (ES); Miguel Rodriguez Manotas, Torres de Cotillas (ES); Javier Fernandez Mateos, Salamanca (ES); Juan Carlos Gallar Ruiz, Torres de Cotillas (ES); David Florenciano Gomez, Torres de Cotillas (ES)

(73) Assignees: ALZHEIMUR 2012 S.L., Murcia (ES); FUNDACION UNIVERSITARIA SAN ANTONIO, Guadalupe (ES); IBSAL (INSTITUTO DE INVESTIGACION BIOMEDICA DE SALAMANC, Salamanca (ES); UNIVERSIDAD DE SALAMANCA, Salamanca (ES)

( * ) Notice: Subject to any disclaimer, the term of this patent is extended or adjusted under 35 U.S.C. 154(b) by 274 days.

(21) Appl. No.: 16/636,416

(22) PCT Filed: Aug. 3, 2018

(86) PCT No.: PCT/ES2018/070544
§ 371 (c)(1),
(2) Date: Feb. 4, 2020

(87) PCT Pub. No.: WO2019/025659
PCT Pub. Date: Feb. 7, 2019

(65) Prior Publication Data
US 2020/0354470 A1    Nov. 12, 2020

(30) Foreign Application Priority Data
Aug. 4, 2017   (EP) ..................... 17382546

(51) Int. Cl.
C07K 16/30    (2006.01)
C07K 16/38    (2006.01)
A61K 39/395   (2006.01)
A61K 39/00    (2006.01)

(52) U.S. Cl.
CPC .............. *C07K 16/30* (2013.01); *C07K 16/38* (2013.01); *A61K 2039/505* (2013.01); *C07K 2317/24* (2013.01); *C07K 2317/34* (2013.01); *C07K 2317/73* (2013.01)

(58) Field of Classification Search
CPC ........ C07K 16/28; C07K 16/30; C07K 16/38; C07K 2317/24; C07K 2317/34; C07K 2317/73; A61K 2039/505; A61K 39/395
See application file for complete search history.

(56) References Cited

U.S. PATENT DOCUMENTS

2009/0305946 A1* 12/2009 Dewji .................... A61K 38/08
435/375

FOREIGN PATENT DOCUMENTS

ES           2 530 141 A2    2/2015

OTHER PUBLICATIONS

Goel et al., Plasticity within the Antigen Combining Site May Manifest as Molecular Mimicry in the Humoral Immune Response, The Journal of Immunology, 2004, 173(12):7358-7367.*
Lloyd et al., Modelling the human immune response: performance of a 1011 human antibody repertoire against a broad panel of therapeutically relevant antigens, Protein Engineering, Design & Selection, 2009, 22(3):159-168.*
Padlan, X-Ray Crystallography of Antibodies, Advances in Protein Chemistry, 1996, 49:57-133.*
Berglund et al., The epitope space of the human proteome, Protein Science, 2008, 17:606-613.*
Edwards et al., The remarkable flexibility of the human antibody repertoire; isolation of over one thousand different antibodies to a single protein, BlyS. Journal of Molecular Biology, 2003, 334:103-118.*
Cancer information from National Institute of Cancer, Apr. 29, 2010, pp. 1-2.*
Vogelstein et al. Nature Medicine, 2004, 10(8): 789-799.*
Hayashi et al., Oncogene, 2012, 31:787-798.*
English translation of ES2530141 (Gallar Ruiz et al., pub. date: Feb. 26, 2015).*
Clinical Study NCT01872598, first posted on Jun. 6, 2013.*
Adenis et al., Annals of Oncology, 2014, 25:1762-1769.*
International Search Report and Written Opinion of the International Searching Authority dated Jan. 22, 2019 in corresponding International application No. PCT/ES2018/070544; 10 pages.
Takagi-Niidome, et al. "Inhibition of [gamma]-Secretase Activity by a Monoclonal Antibody against the Extracellular Hydrophilic Loop of Presenilin 1", Biochemistry, 2013, pp. 61-69, vol. 52; 9 pages.

* cited by examiner

*Primary Examiner* — Hong Sang
(74) *Attorney, Agent, or Firm* — Maier & Maier, PLLC

(57) ABSTRACT

An antibody or fragment thereof, against presenilin, and more specifically against the luminal loop 1 of presenilin, for use in the treatment of cancer, by way of administrating a therapeutically effective quantity of the antibody or a fragment thereof, or a pharmaceutical composition comprising thereof, to a subject who suffers from cancer.

4 Claims, 6 Drawing Sheets
Specification includes a Sequence Listing.

A

B

SEQUENCE LISTING

```
<160> NUMBER OF SEQ ID NOS: 5

<210> SEQ ID NO 1
<211> LENGTH: 8
<212> TYPE: PRT
<213> ORGANISM: Artificial Sequence
<220> FEATURE:
<223> OTHER INFORMATION: Residues 14 to 21 of the amino acid sequence of
      the luminal loop 1(LL1) of the first luminal region (RL1) of
      presenilin 1 or 2.

<400> SEQUENCE: 1

Leu Ile Tyr Thr Pro Phe Thr Glu
1               5

<210> SEQ ID NO 2
<211> LENGTH: 467
<212> TYPE: PRT
<213> ORGANISM: Homo sapiens

<400> SEQUENCE: 2

Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
                20                  25                  30

Arg Glu Arg Gln Glu His Asn Asp Arg Arg Ser Leu Gly His Pro Glu
            35                  40                  45

Pro Leu Ser Asn Gly Arg Pro Gln Gly Asn Ser Arg Gln Val Val Glu
        50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
                100                 105                 110

Leu Ile Tyr Thr Pro Phe Thr Glu Asp Thr Glu Thr Val Gly Gln Arg
            115                 120                 125

Ala Leu His Ser Ile Leu Asn Ala Ala Ile Met Ile Ser Val Ile Val
        130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175
```

```
Phe Ser Phe Ile Tyr Leu Gly Glu Val Phe Lys Thr Tyr Asn Val Ala
                180                 185                 190

Val Asp Tyr Ile Thr Val Ala Leu Leu Ile Trp Asn Phe Gly Val Val
            195                 200                 205

Gly Met Ile Ser Ile His Trp Lys Gly Pro Leu Arg Leu Gln Gln Ala
        210                 215                 220

Tyr Leu Ile Met Ile Ser Ala Leu Met Ala Leu Val Phe Ile Lys Tyr
225                 230                 235                 240

Leu Pro Glu Trp Thr Ala Trp Leu Ile Leu Ala Val Ile Ser Val Tyr
                245                 250                 255

Asp Leu Val Ala Val Leu Cys Pro Lys Gly Pro Leu Arg Met Leu Val
            260                 265                 270

Glu Thr Ala Gln Glu Arg Asn Glu Thr Leu Phe Pro Ala Leu Ile Tyr
        275                 280                 285

Ser Ser Thr Met Val Trp Leu Val Asn Met Ala Glu Gly Asp Pro Glu
290                 295                 300

Ala Gln Arg Arg Val Ser Lys Asn Ser Lys Tyr Asn Ala Glu Ser Thr
                310                 315                 320
305

Glu Arg Glu Ser Gln Asp Thr Val Ala Glu Asn Asp Asp Gly Gly Phe
            325                 330                 335

Ser Glu Glu Trp Glu Ala Gln Arg Asp Ser His Leu Gly Pro His Arg
        340                 345                 350

Ser Thr Pro Glu Ser Arg Ala Ala Val Gln Glu Leu Ser Ser Ser Ile
355                 360                 365

Leu Ala Gly Glu Asp Pro Glu Glu Arg Gly Val Lys Leu Gly Leu Gly
                375                 380
370

Asp Phe Ile Phe Tyr Ser Val Leu Val Gly Lys Ala Ser Ala Thr Ala
            390                 395                 400
385

Ser Gly Asp Trp Asn Thr Thr Ile Ala Cys Phe Val Ala Ile Leu Ile
        405                 410                 415

Gly Leu Cys Leu Thr Leu Leu Leu Leu Ala Ile Phe Lys Lys Ala Leu
                425                 430
        420

Pro Ala Leu Pro Ile Ser Ile Thr Phe Gly Leu Val Phe Tyr Phe Ala
        435                 440                 445

Thr Asp Tyr Leu Val Gln Pro Phe Met Asp Gln Leu Ala Phe His Gln
    450                 455                 460

Phe Tyr Ile
465

<210> SEQ ID NO 3
<211> LENGTH: 448
<212> TYPE: PRT
<213> ORGANISM: Homo sapiens

<400> SEQUENCE: 3

Met Leu Thr Phe Met Ala Ser Asp Ser Glu Glu Val Cys Asp Glu
1               5                   10                  15

Arg Thr Ser Leu Met Ser Ala Glu Ser Pro Thr Pro Arg Ser Cys Gln
                20                  25                  30

Glu Gly Arg Gln Gly Pro Glu Asp Gly Glu Asn Thr Ala Gln Trp Arg
            35                  40                  45

Ser Gln Glu Asn Glu Glu Asp Gly Glu Glu Asp Pro Asp Arg Tyr Val
        50                  55                  60

Cys Ser Gly Val Pro Gly Arg Pro Pro Gly Leu Glu Glu Glu Leu Thr
65                  70                  75                  80
```

-continued

```
Leu Lys Tyr Gly Ala Lys His Val Ile Met Leu Phe Val Pro Val Thr
                85                  90                  95
Leu Cys Met Ile Val Val Ala Thr Ile Lys Ser Val Arg Phe Tyr
            100                 105                 110
Thr Glu Lys Asn Gly Gln Leu Ile Tyr Thr Pro Phe Thr Glu Asp Thr
            115                 120                 125
Pro Ser Val Gly Gln Arg Leu Leu Asn Ser Val Leu Asn Thr Leu Ile
        130                 135                 140
Met Ile Ser Val Ile Val Met Thr Ile Phe Leu Val Val Leu Tyr
145                 150                 155                 160
Lys Tyr Arg Cys Tyr Lys Phe Ile His Gly Trp Leu Ile Met Ser Ser
                165                 170                 175
Leu Met Leu Leu Phe Leu Phe Thr Tyr Ile Tyr Leu Gly Glu Val Leu
            180                 185                 190
Lys Thr Tyr Asn Val Ala Met Asp Tyr Pro Thr Leu Leu Leu Thr Val
            195                 200                 205
Trp Asn Phe Gly Ala Val Gly Met Val Cys Ile His Trp Lys Gly Pro
210                 215                 220
Leu Val Leu Gln Gln Ala Tyr Leu Ile Met Ile Ser Ala Leu Met Ala
225                 230                 235                 240
Leu Val Phe Ile Lys Tyr Leu Pro Glu Trp Ser Ala Trp Val Ile Leu
                245                 250                 255
Gly Ala Ile Ser Val Tyr Asp Leu Val Ala Val Leu Cys Pro Lys Gly
                260                 265                 270
Pro Leu Arg Met Leu Val Glu Thr Ala Gln Arg Asn Glu Pro Ile
            275                 280                 285
Phe Pro Ala Leu Ile Tyr Ser Ser Ala Met Val Trp Thr Val Gly Met
            290                 295                 300
Ala Lys Leu Asp Pro Ser Ser Gln Gly Ala Leu Gln Leu Pro Tyr Asp
305                 310                 315                 320
Pro Glu Met Glu Glu Asp Ser Tyr Asp Ser Phe Gly Glu Pro Ser Tyr
                325                 330                 335
Pro Glu Val Phe Glu Pro Pro Leu Thr Gly Tyr Pro Gly Glu Glu Leu
            340                 345                 350
Glu Glu Glu Glu Glu Arg Gly Val Lys Leu Gly Leu Gly Asp Phe Ile
            355                 360                 365
Phe Tyr Ser Val Leu Val Gly Lys Ala Ala Ala Thr Gly Ser Gly Asp
370                 375                 380
Trp Asn Thr Thr Leu Ala Cys Phe Val Ala Ile Leu Ile Gly Leu Cys
385                 390                 395                 400
Leu Thr Leu Leu Leu Leu Ala Val Phe Lys Lys Ala Leu Pro Ala Leu
                405                 410                 415
Pro Ile Ser Ile Thr Phe Gly Leu Ile Phe Tyr Phe Ser Thr Asp Asn
            420                 425                 430
Leu Val Arg Pro Phe Met Asp Thr Leu Ala Ser His Gln Leu Tyr Ile
            435                 440                 445
```

<210> SEQ ID NO 4
<211> LENGTH: 35
<212> TYPE: PRT
<213> ORGANISM: Artificial Sequence
<220> FEATURE:
<223> OTHER INFORMATION: Luminal Loop 1 of the first luminal region of presenilin 1

```
<400> SEQUENCE: 4

Ile Lys Ser Val Ser Phe Tyr Thr Arg Lys Asp Gly Gln Leu Ile Tyr
1               5                   10                  15

Thr Pro Phe Thr Glu Asp Thr Glu Thr Val Gly Gln Arg Ala Leu His
            20                  25                  30

Ser Ile Leu
        35

<210> SEQ ID NO 5
<211> LENGTH: 35
<212> TYPE: PRT
<213> ORGANISM: Artificial Sequence
<220> FEATURE:
<223> OTHER INFORMATION: Luminal Loop 1 of the first luminal region of
      presenilin 2

<400> SEQUENCE: 5

Ile Lys Ser Val Arg Phe Tyr Thr Glu Lys Asn Gly Gln Leu Ile Tyr
1               5                   10                  15

Thr Pro Phe Thr Glu Asp Thr Pro Ser Val Gly Gln Arg Leu Leu Asn
            20                  25                  30

Ser Val Leu
        35
```

ANTI-PRESENILIN ANTIBODY FOR USE IN THE PREVENTION AND/OR TREATMENT OF CANCER

STATEMENT REGARDING SEQUENCE LISTING

The instant application contains a Sequence Listing that is hereby incorporated by reference in its entirety. An ASCII copy of the Sequence Listing, named Sequence_Listing_EN.txt, submitted on Apr. 21, 2020 is 9.45 kb in size, and includes no new matter.

FIELD

The present invention relates to anti-presenilin antibodies for use in the treatment of cancer. Therefore, the present invention falls within the medicine sector, more specifically, in the sector of molecular biology applied to medicine, pharmacology and oncology.

BACKGROUND

According to data from the World Health Organization (WHO), cancer causes approximately 8 million deaths per year, making it the leading cause of death worldwide. In fact, it is expected that from now until 2035 nearly 15 million deaths per year will be related to tumors.

Cancer is treated with different approaches, normally combined, that can be classified into the following major groups: biological therapies, chemotherapy, hormonal therapy, radiotherapy, stem cell and bone marrow transplants, surgery, and support therapies (i.e. biphosphonates, erythropoietin, hematopoietic growth factors, steroids and platelet transfusions). Biological therapy, also known as immunotherapy, uses substances that the body naturally produces to destroy cancerous cells. There are different types of treatments, including monoclonal antibodies, cancer growth inhibitors, angiogenesis inhibitors, vaccines and gene therapy, among others. immunotherapy is directed at a wide range of targets.

Knowledge of different molecular pathways, characteristics of different tumors, as well as the physiology of tumor cells, has made it possible to design new drugs to block the action of different proteins involved in the different signal transduction pathways critical to cell growth and division. Some of the best characterized pathways are those mediated by receptors of the tyrosine kinase (TK) protein family, one of the main members of this family being the EGFR growth factor (epidermal growth factor receptor), which includes EGFR/HER1, ErbB-2/HER2, ErbB-3/HER3 and ErbB-4/HER4 receptors, mainly involved in the MAPK (mitogen-activated protein kinase) signaling pathways, the PI3K (phosphoinositide 3-kinase) pathway, which contributes to cell cycle progression, reduces apoptosis and promotes cancer cell metastasis, and the JAK/STAT pathways and phospholipase C 1 gamma (PLCyl), related to cell proliferation, differentiation, migration and apoptosis. Other members of this family also include PDGFR (platelet-derived growth factor receptor alpha), FGFR (fibroblast growth factor receptor) and VEGFR (vascular endothelial growth factor receptor) proteins. The receptors of this family are frequently involved in human and animal neoplasia and only one tumor cell can overexpress more than one type of these receptors. Inhibitors of tyrosine kinase activity, such as gefitinib, erlotinib and lapatinib, as well as monoclonal antibodies against the extracellular domain of the receptor, have been developed for these receptors. Among the monoclonal antibodies approved for use in oncology, trastuzumab is an anti-ErbB2/HER2 for breast cancer, cetuximab is an anti-ErbB1/EGFR for colon cancer, and bevacizumab is an anti-VEGF for colorectal, breast and lung cancers (cf. G. Adams et al., Nature Biotechnology 2005, vol. 23, pp. 1147-57). Multi-target inhibitors (such as Sutent) inhibit the tyrosine kinase activity of VEGFR, PDGFR and FGFR.

Alternatively, different immunotherapies based on humanized monoclonal antibodies have been developed based on the MUC1 protein. MUC1 has been used as a tumor marker for therapeutic monitoring in patients with breast cancer, known as the CA15.3 marker; it is found to be 10 to 15 times higher in patients with metastatic cancer, although the prognostic value thereof is only important when it is analyzed in combination with other parameters. Among the monoclonal antibodies designed against MUC1, huBrE-3 and R-1549 (pemtumomab), used in combined radioimmunotherapy treatments for breast cancer and other cancers with promising results are worth noting.

Furthermore, it has also been observed that the immune system cells associated with the tumor microenvironment express a greater number of receptors, such as CTLA4 (cytotoxic T-lymphocyte antigen 4) and PD1 (programmed death-1), involved in the down-regulation of lymphocyte activation and immunological tolerance. Blocking CTLA4 receptors by means of antibodies directed against them or the ligands thereof favor anti-tumor immunity; and for that reason, the FDA (Food and Drug Administration) approved the use of some of these antibodies, such as ipilimumab, as complementary therapy for cancer.

However, most of these therapies, which are usually complementary to already known treatments, and newly designed chemotherapy agents, have given rather modest results in the locally advanced disease and in the metastatic state. Therefore, developing new strategies to prevent and/or treat cancer continues to be necessary, focusing said strategies on the search for new therapeutic targets.

SUMMARY

Inventors have discovered the usefulness of an anti-presenilin antibody, or a fragment thereof, for use in the prevention and/or treatment of cancer. Specifically, inventors have demonstrated that the use of an anti-presenilin antibody or a fragment thereof, specifically an antibody, or fragment thereof, capable of binding to the antigen that comprises the amino acid sequence SEQ ID NO: 1 [LIYTPFTE] of the presenilin, is useful in the prevention and/or treatment of cancer.

Presenilins are transmembrane proteins whose genes, preferably in humans, show high homology to each other (80% nucleotide identity). In the present invention, "presenilin" is therefore understood as presenilin 1, which comprises SEQ ID NO: 2, or presenilin 2, which comprises SEQ ID NO: 3.

The term "antigen" for the purposes of the present invention relates to a predetermined region to which the antibody can be selectively bonded. The antigen can be a polypeptide, a carbohydrate, a nucleic acid, a lipid, a hapten or another natural or synthetic molecule. Preferably, the antigen is a polypeptide; more preferably, the antigen comprises SEQ ID NO: 1.

Thus, in a first aspect, the present invention relates to an antibody or a fragment thereof that specifically binds to the amino acid sequence that comprises SEQ ID NO: 1 [LIYTPFTE] of the presenilin for use in the prevention and/or treatment of cancer in a subject. Alternatively, the present invention relates to the use of an antibody or a fragment thereof that specifically binds to the amino acid sequence that comprises SEQ ID NO: 1 [LIYTPFTE] of the presenilin for the preparation of a medicament or pharmaceutical composition for the prevention and/or treatment of cancer in a subject.

In a preferred embodiment, the presenilin is selected from presenilin 1 which comprises SEQ ID NO: 2, or presenilin 2 which comprises SEQ ID NO: 3.

In a preferred embodiment, the use of the antibody described in the present invention is useful in the prevention and/or treatment of tumors by inhibiting the growth of the tumor cells, which is a consequence of the inhibition and/or reduction of the expression of proteins such as NOTCH.

One of the advantages of using an anti-presenilin antibody that specifically binds to the SEQ ID NO: 1 for the prevention and/or treatment of cancer, as described in the present document, is that said antibody does not pass through the blood-brain barrier, thus avoiding the adverse effects of said event.

The peptide of sequence SEQ ID NO: 1 is an eight-amino acid peptide that corresponds to the residues 14 to 21 of the amino acid sequence of the luminal loop 1 (LL1) of the first luminal region (RL1) of presenilin 1 or presenilin 2. LL1 of RL1 of presenilin 1 comprises the amino acid sequence SEQ ID NO: 4. LL1 of RL1 of presenilin 2 comprises the amino acid sequence SEQ ID NO: 5.

Another aspect of the invention relates to the use of the peptide of SEQ ID NO: 1 as a pharmacological target to screen useful molecules in the prevention and/or treatment of cancer.

For the purposes of the present invention, the term "antibody" refers to immunoglobulin molecules, or immunologically active portions of immunoglobulin molecules, i.e. molecules containing an antigen binding site specifically bonded (immunoreacts) with LL1 of RL1 of presenilin 1 (SEQ ID NO: 2) or presenilin 2 (SEQ ID NO: 3), and more specifically to the peptide of SEQ ID NO: 3, which comprises the amino acid SEQ ID NO: 5. Examples of portions of immunologically active immunoglobulin molecules comprise fragments F(ab) and F(ab')2, which may be generated by treating the antibody with an enzyme, such as pepsin, or recombinantly.

In a preferred embodiment, the antibody of the invention can be polyclonal (typically comprising different antibodies directed against different determinants or epitopes) or monoclonal (directed against a single determinant in the antigen). The expression "monoclonal antibody" refers to a population of antibody molecules containing only one kind of antigen binding site capable of immunoreacting with a particular epitope of the antigen. The monoclonal antibody may be biochemically altered by genetic manipulation or may be synthetic, the antibody possibly lacking, in its totality or in parts, portions that are not necessary for the recognition of the antigen. In a preferred embodiment, the antibody for use, according to the present invention, is preferably a polyclonal antibody.

In another preferred embodiment of the use of the antibody as described in the present invention, it is characterized in that it may be a recombinant, humanized, chimerical or synthetic antibody, or a combination thereof. A "recombinant antibody" (rAB) is an antibody which has been produced in a host cell that has been transformed or transfected with a polynucleotide that encodes for the peptide that comprises SEQ ID NO: 1, with nucleic acid encoding for the antibody of the invention, or which produces the antibody that is specifically bonded to SEQ ID NO: 1, or the peptide of SEQ ID NO: 1, as a result of the homologous recombination. A "chimerical antibody" is an antibody wherein a region of the heavy and/or light chain is identical to or homologous with the corresponding antibody sequences from a determined species or belonging to a class or subclass of determined antibodies, whilst the remaining chain(s) is(are) identical to or homologous with the corresponding sequences in antibodies derived from other species or belonging to another class or subclass of antibodies, as well as fragments of said antibodies, so that they demonstrate the desired biological activity.

The term "treatment" as understood in the present invention relates to combating the effects caused by the disease or pathological condition of interest in a subject (preferably mammal, and more preferably, a human), which comprises:
  (i) inhibiting the disease or pathological condition, in other words, stopping the development thereof;
  (ii) alleviating the disease or pathological condition, in other words, causing the disease or pathological condition or symptoms thereof to regress;
  (iii) stabilizing the disease or the pathological condition.

The term "prevention" as understood in the present invention consists of preventing the onset of the disease, in other words, preventing the disease or pathological condition from occurring in a subject (preferably mammal, and more preferably a human), in particular, when said subject has a predisposition to the pathological condition, but still has not been diagnosed with it.

For the purposes of the present invention, the term "cancer" relates to a malignant tumor of potentially unlimited growth that is spread locally by invasion or systematically by metastasis. The term cancer in the present invention includes solid tumors, as well as hematologic tumors, such as leukemias, lymphomas and myelodysplastic syndromes. According to the present invention, the antibody or fragment hereof that specifically bind to SEQ ID NO: 1 of presenilin, preferably to human presenilin, is administrated to individuals with cancer.

In a preferred embodiment of the antibody for use as described in the invention, it is characterized in that the cancer comprises solid and/or hematologic tumors, such as leukemias, lymphomas and myelodysplastic syndromes.

In another preferred embodiment, the cancer is selected from the list consisting of lung cancer, non-small cell lung cancer, small cell lung cancer, bone cancer, pancreatic cancer, skin cancer, head or neck cancer, cutaneous melanoma, uterine cancer, ovarian cancer, rectal cancer, gastric cancer, colon cancer, breast cancer, Fallopian tube carcinoma, endometrial carcinoma, cervical carcinoma, vaginal carcinoma, vulvar carcinoma, esophageal cancer, small intestine cancer, urethral cancer, prostate cancer, bladder cancer, kidney or ureter cancer, renal cell carcinoma, central (CNS) and peripheral nervous system tumors, spinal cord tumors, brainstem glioma, glioblastoma multiforme, astrocytoma, medulloblastomas, meningiomas, squamous cell carcinoma and/or pituitary adenoma, lymphomas and leukemias. In a particular embodiment, the cancer is preferably breast cancer, head and neck cancer, colon cancer, prostate cancer, glioblastoma, lymphomas and/or leukemias.

The term "subject" or "patient", as used herein, relates to all animals classified as mammals and comprises, but is not restricted to, domestic and farm animals, primates and humans, for example, human beings, non-human primates, cows, horses, pigs, sheep, goats, dogs, cats or rodents. Preferably, the subject is a male or female human of any age or race.

Another aspect of the present invention relates to a medicament or pharmaceutical composition that comprises the anti-presenilin antibody, as described previously, along with a pharmacologically acceptable carrier and/or excipient, for use in the prevention and/or treatment of cancer. Alternatively, the present invention relates to the use of a medicament or pharmaceutical composition that comprises the anti-presenilin antibody, as described previously, along with a pharmacologically acceptable carrier and/or excipient, for the preparation of a medicament or pharmaceutical composition in the prevention and/or treatment of cancer.

The term "medicament" or "pharmaceutical composition", used interchangeably throughout the present document, as used in the present description, refers to any substance or combination of substances presented as having properties for treating or preventing disease in organisms, preferably human beings, or which may be used or administered to organisms, preferably human beings, with the aim of restoring, correcting or modifying physiological functions by carrying out a pharmacological, immunological or metabolic action. The medicament or pharmaceutical composition of the invention can be used alone or in combination with other medicinal products or compositions to prevent and/or improve cancer as a combined therapy, being able to be administered at the same time or at different times. Production of the pharmaceutical composition can be carried out by any of the methods known and described in the state of the art.

The "pharmaceutically acceptable carrier" refers to a substance that is used in the composition to dilute any of the compounds comprised therein to a determined volume or weight. The pharmaceutically acceptable carrier is an inert substance or a substance with action similar to any of the elements comprised in the composition of the present invention. The function of the carrier is to facilitate the incorporation of other elements, to allow better dosing and administration or to give consistency and shape to the composition. Water or aqueous saline solutions and aqueous dextrose and glycerol solutions are preferably used as carriers, particularly for injectable solutions. The term "excipient" refers to a substance that helps to absorb the elements of the composition of the invention, stabilizes said elements, activates or helps to prepare the composition in the sense of giving it consistency or providing flavors that make it more pleasant. Thus, excipients could have the function of keeping the ingredients bonded together, such as in the case of starches, sugars or celluloses, the sweetening function, the colorant function, the function of protecting the composition, such as for example isolating it from air and/or moisture, the filler function for a tablet, capsule or any other form of formulation, the disintegrating function to facilitate the dissolution of the components and their absorption in the intestine, without excluding other types of excipients not mentioned in this paragraph. Preferably, the "pharmaceutically acceptable carriers and/or adjuvants" are approved by the regulatory agency of a state government or a federal government, or are listed in the United States Pharmacopoeia or other pharmacopoeia recognized in general for use in animals and, more particularly, in human beings. Said compounds are widely known in the state of the art.

Both the antibody described in the present invention and the pharmaceutical composition comprising thereof are used in a therapeutically effective quantity, "therapeutically effective quantity" being understood as the level, quantity or concentration of the antibody of the present invention or of the pharmaceutical composition comprising thereof, which produces the desired effect in preventing and/or treating cancer, preferably inhibiting their growth, without causing adverse effects. Dosing to obtain a therapeutically effective quantity depends on a variety of factors, such as for example, age, weight, gender or tolerance of the individual to whom the antibody or pharmaceutical composition of the invention will be administered.

The pharmaceutical composition of the present invention can be formulated by their administration in a variety of forms known in the state of the art. Examples of preparations include any solid composition (tablets, pills, capsules, granules, etc.) or liquid composition (solutions, suspensions or emulsions) for oral, topical or parenteral administration. The composition of the present invention can also be in the form of sustained-release formulations of drugs or any other conventional release system, such that it can be contained in, but not limited to, nanoparticles, liposomes or nanospheres, in a polymeric material, in a biodegradable or non-biodegradable implant or in biodegradable microparticles, such as for example, biodegradable microspheres. In a particular embodiment of the pharmaceutical composition for use according to the invention, the composition is formulated for the oral, parenteral, intravenous or intratumoral administration thereof.

Said composition and/or formulations thereof can be administered to an animal, including a mammal, and therefore to humans, in a variety of forms, including, but not limited to, intraperitoneal, intravenous, intradermal, intraspinal, intrastromal, intrasynovial, intralesional, intraarterial, intramuscular, intranasal, intracraneal, subcutaneous, intracapsular, oral, enteral, parenteral, topical, by means of transdermal patches, percutaneous, nasal spray, surgical implant or infusion pump. One preferred route of administration of the invention for the treatment and/or prevention of cancer is intravenous administration.

In another particular embodiment of the uses of the pharmaceutical composition of the invention, the composition is characterized in that it further comprises an anti-tumor agent.

"Anti-tumor agent" or "chemotherapeutic agent", used interchangeably throughout the present document, is understood to be any substance capable of inhibiting cell proliferation or capable of inducing cell death. The agents capable of inhibiting cell proliferation without causing cell death are generally called cytostatic agents, while those capable of inducing cell death normally by activating apoptosis are generally called cytotoxic agents. Non-limiting examples of anti-tumor agents suitable for use in the composition of the invention include, but are not limited to, (i) microtubule-stabilizing agents such as taxanes, paclitaxel, docetaxel, epothilones and laulimalides, (ii) kinase inhibitors such as Iressa®, Gleevec, Tarceva™, (Erlotinib HCl), BAY-43-9006, (iii) specific antibodies for receptors with kinase activity including, but not limited to, Trastuzumab (Herceptin®), Cetuximab (Erbitux®), Bevacizumab (Avastin™), Rituximab (Ritusan®), Pertuzumab (Omnitarg™); (iv) inhibitors of the mTOR route such as rapamycin and CCI-778; (v) Apo2L1Trail, (vi) anti-angiogenic agents such as endostatin, combretastatin, angiostatin, thrombospondin and the vascular endothelial growth inhibitor (VEGI); (vii) anti-neoplastic vaccines including activated T cells, non-specific immunopotentiator agents (for example, interferons, interleukins); (viii) antibiotic cytotoxic agents such as doxorubicin, bleomycin, dactinomycin, daunorubicin, epirubicin, mitomycin, mitoxantrone, etc.; (ix) alkylating agents such as Melphalan, Carmustine, Lomustine, cyclophosphamide, ifosfamide, Chlorambucil, Fotemustine, Busulfan, Temozolomide and thiotepa; (x) hormonal antineoplastic agents such as Nilutamide, cyproterone acetate, anastrozole, Exemestane, Tamoxifen, Raloxifene, Bicalutamide, Aminoglutethimide, leuprorelin acetate, Toremifene citrate, Letrozole, Flutamide, Megestrol acetate and goserelin acetate; (xi) gonadal hormones such as cyproterone acetate and medroxyprogesterone acetate; (xii) antimetabolites such as Cytarabine, Fluorouracil, Gemcitabine, Topotecan, Hydroxyurea, Tioguanine, Methrotrexate, Colaspase, Raltitrexed and Capecitabine; (xiii) anabolic agents such as nandrolone; (xiv) steroid adrenal hormones such as methylprednisolone acetate, dexamethasone, hydrocortisone, prednisolone and prednisone; (xv) antineoplastic agents such as Carboplatin, Cisplatin, Oxaliplatin, Etoposide and Dacarbazine; (xvi) topoisomerase inhibitors such as topotecan and irinotecan; (xvii) epigenetic agents such as histone deacetylase inhibitors, histone methyltransferase inhibitors, histone demethylase inhibitors and DNA methyltransferase inhibitors; and (xviii) autophagy modulating agents such as chloroquine.

In another aspect, the invention relates to a method for preventing and/or treating cancer in a subject, which comprises the administration of a therapeutically effective quantity of antibody or pharmaceutical composition comprising thereof to said subject, as described in the present invention.

The terms and expressions used in the present inventive aspect have been defined in previous inventive aspects. In turn, all particular embodiments previously described in the present invention are applicable to the methods of the invention.

Throughout the description and in the claims, the word "comprises" and variants thereof are not intended to exclude other technical characteristics, additives, components or steps. For persons skilled in the art, other objects, advantages and characteristics of the invention will arise, partly from the description and partly from the implementation of the invention. The following examples and drawings are provided by way of illustration, and are not meant to limit the present invention.

DETAILED DESCRIPTION

Figure 1:
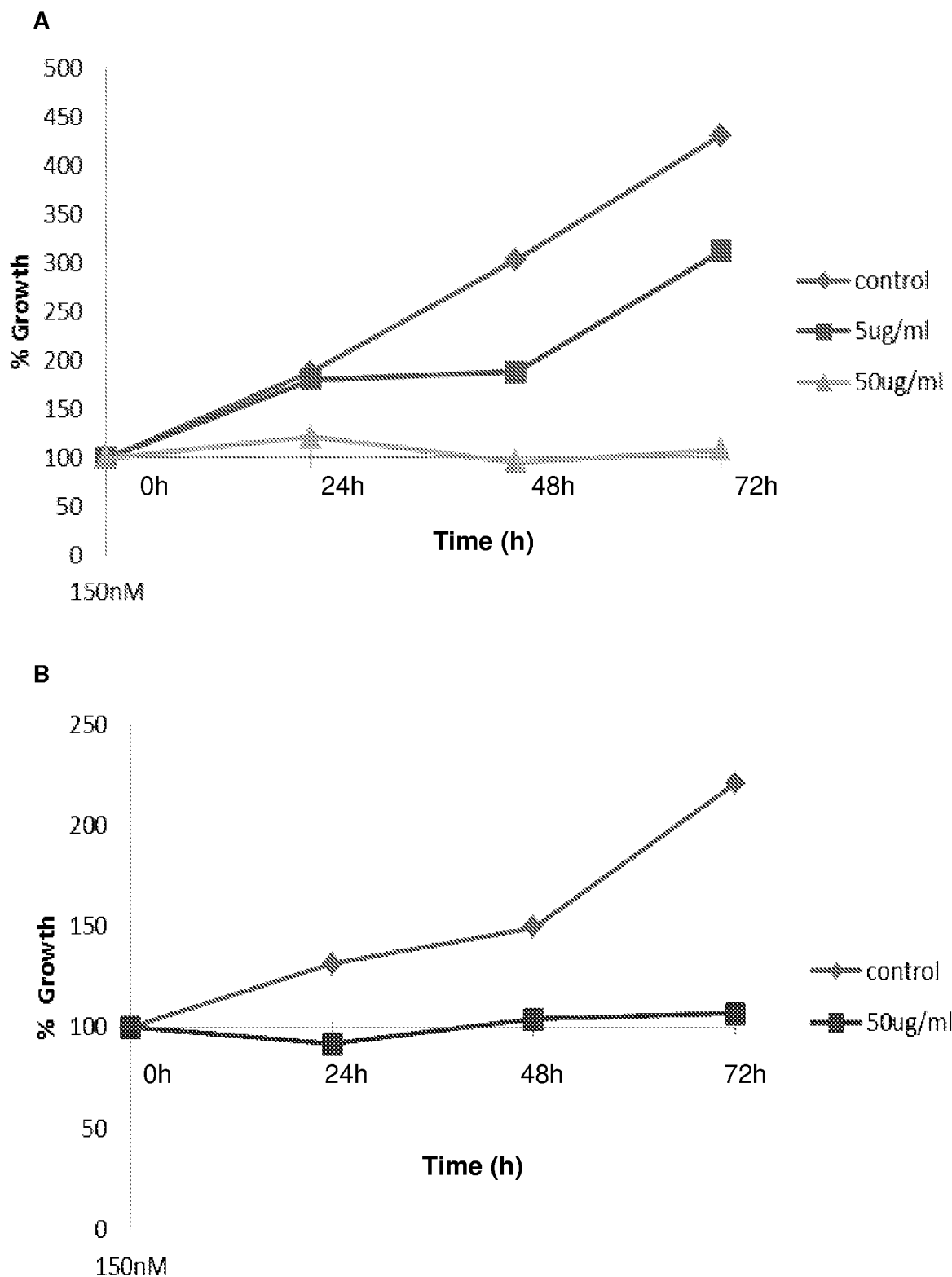
FIG. 1A is a viability analysis of the tumor cell lines MCF7 in the presence of the anti-presenilin 1 polyclonal antibody that specifically binds to SEQ ID NO: 1, to concentrations of 5 and 50 μg/ml, for 0, 24, 48 and 72 hrs, with respect to the control group not treated with said antibody. Cell growth was measured with the MTT assay and is expressed as a percentage with respect to the control cells.
FIG. 1B is viability analysis of the tumor cell lines PC3 in the presence of the antipresenilin 1 polyclonal antibody that specifically binds to SEQ ID NO: 1, to concentrations of 5 and 50 μg/ml, for 0, 24, 48 and 72 hrs, with respect to the control group not treated with said antibody. Cell growth was measured with the MTT assay and is expressed as a percentage with respect to the control cells.
FIG. 1C is viability analysis of the tumor cell lines CAL33 in the presence of the antipresenilin 1 polyclonal antibody that specifically binds to SEQ ID NO: 1, to concentrations of 5 and 50 μg/ml, for 0, 24, 48 and 72 hrs, with respect to the control group not treated with said antibody. Cell growth was measured with the MTT assay and is expressed as a percentage with respect to the control cells.
FIG. 1D is viability analysis of the tumor cell lines HCT116 in the presence of the anti-presenilin 1 polyclonal antibody that specifically binds to SEQ ID NO: 1, to concentrations of 5 and 50 μg/ml, for 0, 24, 48 and 72 hrs, with respect to the control group not treated with said antibody. Cell growth was measured with the MTT assay and is expressed as a percentage with respect to the control cells.
FIG. 1E is viability analysis of the tumor cell lines MEF in the presence of the antipresenilin 1 polyclonal antibody that specifically binds to SEQ ID NO: 1, to concentrations of 5 and 50 μg/ml, for 0, 24, 48 and 72 hrs, with respect to the control group not treated with said antibody. Cell growth was measured with the MTT assay and is expressed as a percentage with respect to the control cells.
Figure 1:
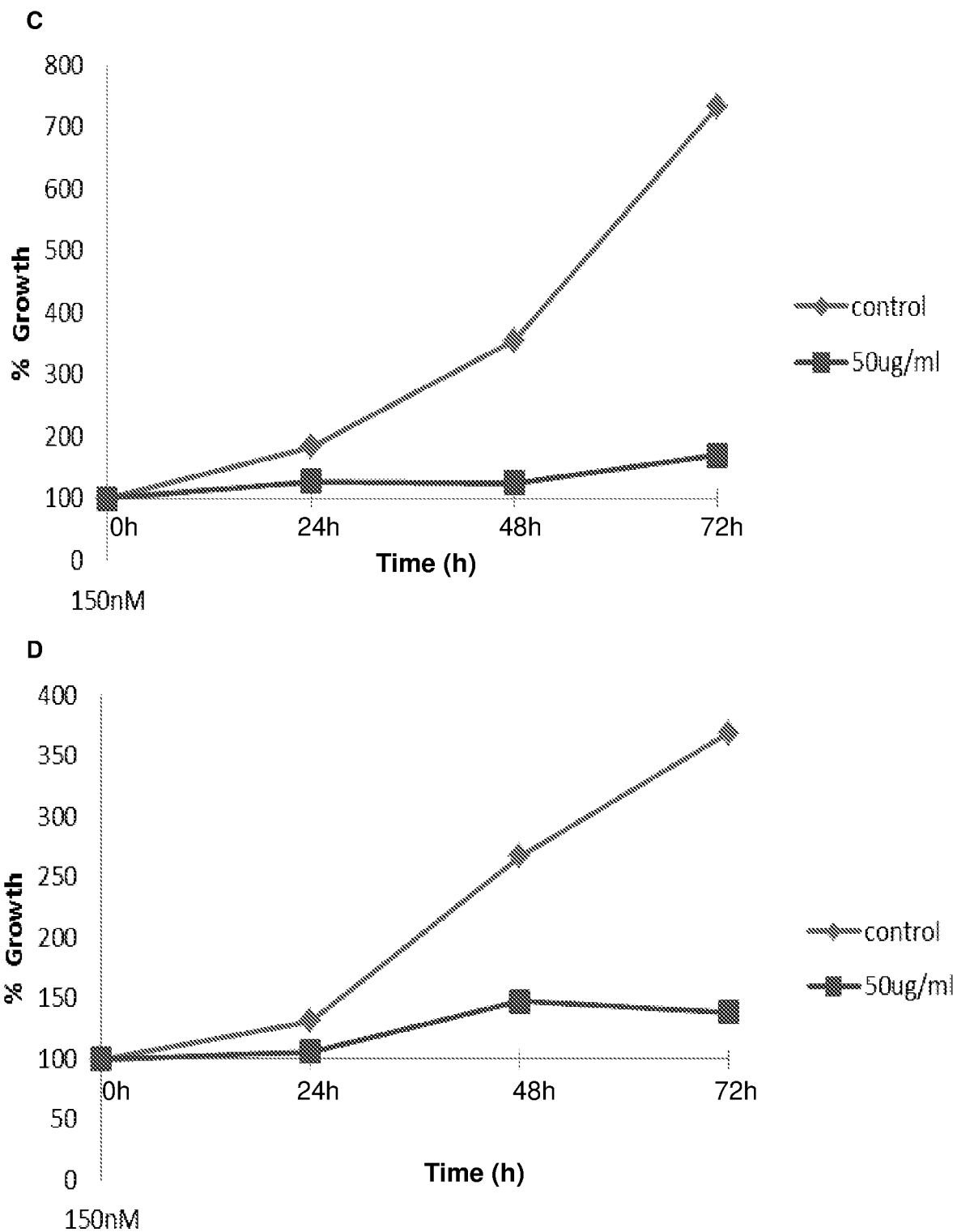
Figure 1:
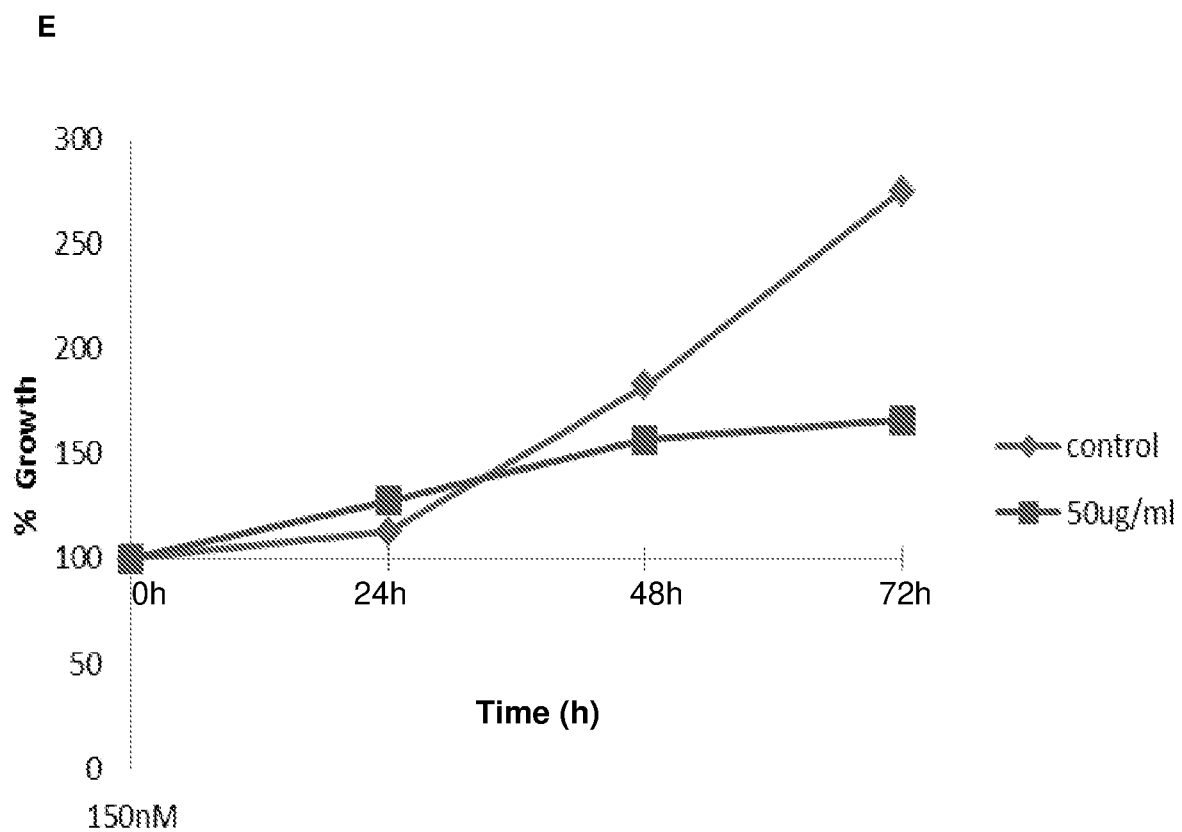

The invention is illustrated below by means of assays carried out by the inventors which reveal the effectiveness of the product of the invention.

The following examples show that the use of a specific antibody against the presenilin protein directed against the LIYTPFTE peptide (SEQ ID NO: 1) which is found within the luminal loop 1 of said protein is useful in the treatment of cancer, since it is capable of inhibiting the proliferation of cultured tumor cells. The anti-presenilin antibody directed against the peptide of SEQ ID NO: 1 used in the following examples is a polyclonal antibody.

Materials and Methods.

Cell Cultures

To demonstrate the capacity to prevent and/or treat cancer, preferably solid tumors, of the antibody described herein, cell lines have been used, all of which are derived from different types of cancer (Table 1).

TABLE 1

List of cell lines used in the examples of the invention. All cell lines have been acquired in the ATCC (American Type Culture Collection).

| Cancer | Cell line | Type |
|---|---|---|
| Breast | MCF7 (ATCC ® HTB-22 ™) | Luminal |
| Head and neck | CAL33 (ACC 447) | Squamous carcinoma |
| Colon | HCT116 (ATCC ® CCL-247 ™) | Epithelial |
| Prostate | PC3 (ATCC ® CRL-1435 ™) | Adenocarcinoma |

In addition to the cell lines of Table 1, the use of the polyclonal antibody of the invention in a primary culture of human fibroblasts (MEF) has been assayed. The culture media used to grow said cell lines were prepared from RPMI and DMEM culture media (Lite Technologies, Carlsbad, CA, USA) supplemented with 10% FBS (fetal bovine serum) (Sigma, St Louis, MO, USA) and 1% penicillin-treptomycin (Invitrogen). All cell lines were cultivated at a temperature of 37° C. and 5% C02, with DMEM, except for the cell line of head and neck cancer (CAL33) which was cultivated in the RPMI medium. They were maintained in a thermostatically-controlled incubator at 37° C., in the presence of 5% C02 and 95% air (moisture-saturated air). Specifically, the monoclonal antibody of the invention was tested in the MCF7 cell line cultured in EMEM medium, under the same conditions mentioned above.

Obtaining the Anti-Presenilin Antibody that Specifically Binds to SEQ ID NO: 1.

SEQ ID NO: 1 is an eight-amino acid peptide that corresponds to the residues 14 to 21 of the amino acid sequence of the luminal loop 1 (LL1) of the first luminal region (RL1) of presenilin 1 or presenilin 2. Said antigenic peptide of SEQ ID NO: 1 was synthesized by means of solid phase techniques and purified by HPLC (high performance liquid chromatography), reaching a purity of 97.21%. The original peptide sequence of SEQ ID NO: 1 was modified, adding a cysteine residue to the N-terminus end of the peptide. The peptide is covalently bonded by means of disulfide bonds to BC ("Blue Carrier Immunogenic Protein" from Pierce).

In order to obtain the polyclonal antibodies tested below, a total of two hens were immunized with the BC-peptide complex and Freund's adjuvant (from Sigma) and boosters were injected at intervals of 14, 28 and 56 days. Eggs from each hen were collected between 40 and 71 days after the start of immunization. The yolks were separated, the lipids were eliminated and the antibodies were precipitated/purified with the Pierce Isolation Kit ("Pierce Chicken IgY Purification Kit" from Thermo Scientific). Two batches of antibodies corresponding to each of the immunized animals were obtained: Polyclonal 1 and Polyclonal 2.

On the other hand, for obtaining of the monoclonal antibodies tested below, techniques widely known in the state of the art, and more specifically in the field of the invention, were used. Throughout the described examples, the monoclonal antibody of the invention will be referred to as moAB.

MTT Cell Viability Assay

MTT 3-(4,5-dimethylthiazol-2-yl)-2,5-diphenyltetrazolium bromide is a tetrazolium salt that has a yellowish color in an aqueous solution. In metabolically active cells, it is reduced in the mitochondrial pathway by the succinate dehydrogenase enzyme (SDH), producing a dark blue hydrophobic compound, formazan, which is soluble in DMSO (dimethyl sulfoxide), producing a solution which has an absorbency measured at 570 nm in a spectrophotometer, the color intensity being proportional to the quantity of metabolically active cells. Therefore, the MTT method is a colorimetric assay that determines cell growth and survival, as well as the cytotoxic effect of any agent on cultured cell lines.

To carry out the MTT assay, 10,000 cells per well (10,000 cel/ml) were placed in tour 24-well plates and were incubated at 37° C. and 5% CO2 for 24 hours to allow for the adherence thereof. Next, different concentrations of polyclonal and monoclonal antibodies, 5 μg/ml and 50 μg/ml, were tested in triplicate at the times of 0, 24, 48 and 72 hours. Cells that were not treated with the antibody were used as a control. Afterwards, the culture medium was removed and 110 μl of MTT were added. After 1 hr at 37° C., the supernatant was aspirated and 1 mi of DMSO was added to dissolve the formazan crystals deposited in the bottom of the wells. Lastly, the absorbencies at 570 nm were determined by means of an Ultra Evolution microplate reader (TecanR).

Western Blot

Figure 2:
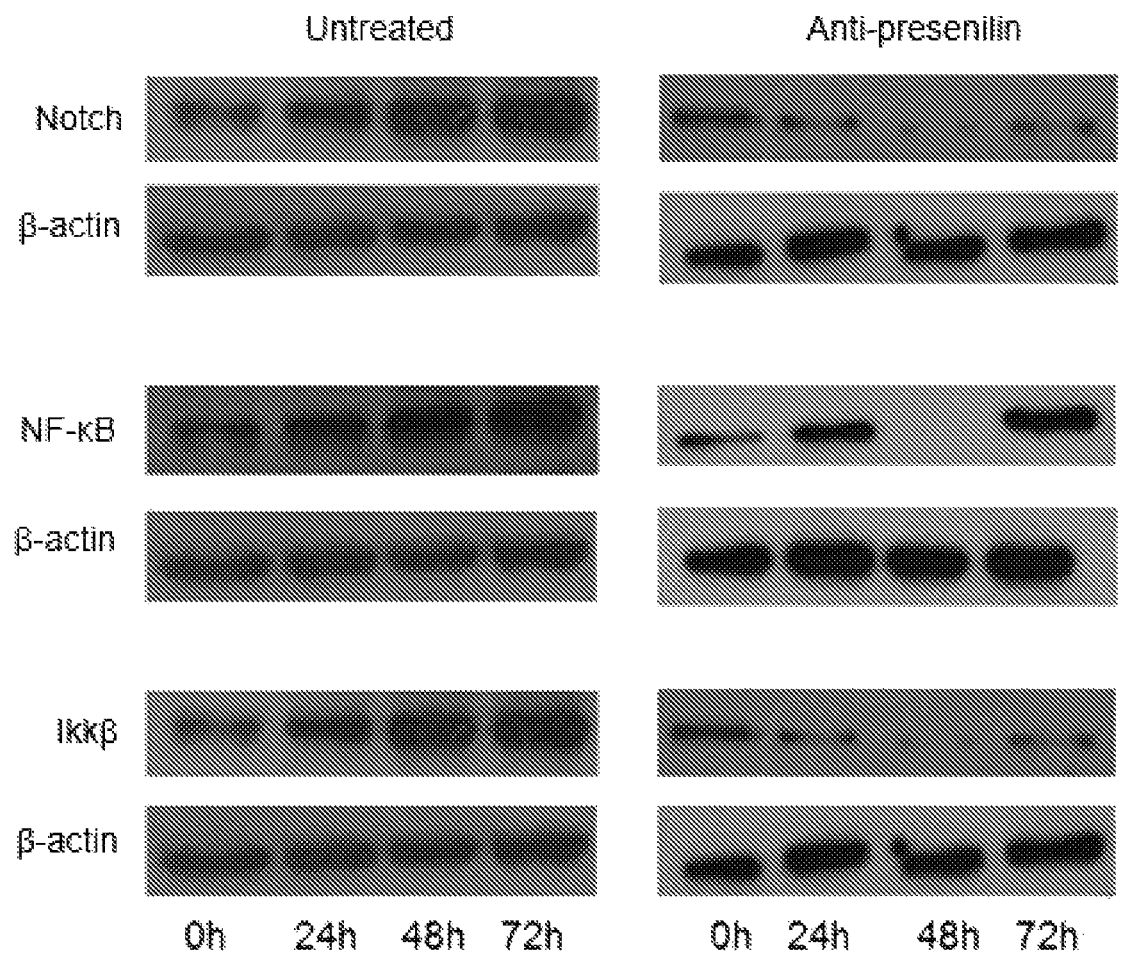
FIG. 2. Western Blot images of NOTCH, NFKb and IKKb proteins in MCF7 cells treated with the anti-presenilin 1 antibody that specifically binds to the SEQ ID NO: 1, to concentrations of 5 and 50 μg/ml, for 0, 24, 48 and 72 hrs, with respect to the control group not treated with the antibody.

The quantity of NOTCH (monoclonal antibody ab52627 of Abcam), NFKB (monoclonal antibody sc.8008 of Santa Cruz Biotechnology) and IKKB (monoclonal antibody D3006 of Cell Signaling) proteins in the MCF7 breast cancer cell line was determined by using the Western-blot (WB) technique. In FIG. 2, Western Blot images representing these proteins are shown in the MCF7 cell line, treated with or without the anti-presenilin antibody used in the invention, at 0, 24, 48 and 72 hours. All antibodies are described in Table 2.

TABLE 2

Antibodies

| Type of antibody | Antibody | Source | Manufacturer | Reference | Dosage used |
|---|---|---|---|---|---|
| Primary | Anti-β-Actin | Mouse | Sigma-Aldrich | A5441 | 1:10000 |
|  | Anti-Notch-1 | Rabbit | ABCAM | ab52627 | 1:2000 |
|  | Anti-NF-κB | Mouse | Santa Cruz Biotechnology | sc8008 | 1:200 |
|  | Anti-Ikkβ | Rabbit | Cell Signaling | 8943S | 1:1000 |
|  | Anti-Notch (extracellular region) | Rabbit | EMD Millipore | ABS90 | 1:500 |
| Secondary | Anti-Mouse | Sheep | Sigma-Aldrich | NXA931V | 1:10000 |
|  | Anti-Rabbit | Goat | EMD Millipore | AP307P | 1:10000 |

Briefly, the cells were collected at the times of study mentioned and the total soluble protein with PBS was extracted in the presence of protease inhibitors (Complete™ Protease Inhibitor Cocktail, Sigma-Aldrich), by means of three freeze-thaw cycles. Once quantified by the Nanodrop 1000 spectrophotometer (Thermo Scientific, USA), 10 micrograms of total soluble protein were subjected to 10% SDS-PAGE and subsequently transferred to a polyvinylidene fluoride membrane. Next, the standard WB was carried out using the concentrations of the monoclonal antibodies suggested by the manufacturer. The image capture of the WB was carried out with the Gel Doc™ XR+ (BioRad) documentation system and the relative quantification of the bands was carried out with the Image Lab v5.2 (BioRad) software. The WB study was repeated in three independent assays. The antibody was used as a positive load control against β-actin.

By way of example, FIG. 2 shows the images of the Western Blot results obtained with the cell line MCF7.

Example 1. The Anti-Presenilin 1 Antibody that Specifically Recognizes SEQ ID NO: 1 Inhibits Tumor Cell Growth The results shown in FIG. 1 demonstrate that the treatment with 50 μg/ml of the anti-presenilin 1 polyclonal antibody that specifically binds to SEQ ID NO: 1 is capable of inhibiting the viability of tumor cell lines from different sources, such as: breast cancer cells (MCF7), prostate cancer cells (PC3), head and neck cancer cells (CAL33), colon cancer cells (HCT116) and the primary culture of fibroblasts (MEF), with respect to the control cells, which are also tumor cells but are not treated with the anti-presenilin polyclonal antibody indicated herein.

Furthermore, as observed in FIG. 2, the treatment with 50 μg/ml of anti-presenilin 1 polyclonal antibody reduces cell viability as a function of time, analyzed by WB. After incubating the MCF7 cells in the presence of the anti-presenilin polyclonal antibody for 72 hrs, expression of the NOTCH, NFKB and Ikkl3 proteins is inhibited. The absence of the expression of NOTCH and the proteins of the NFKB pathway may be responsible for reducing the viability of the tumor cells.

Figure 3:
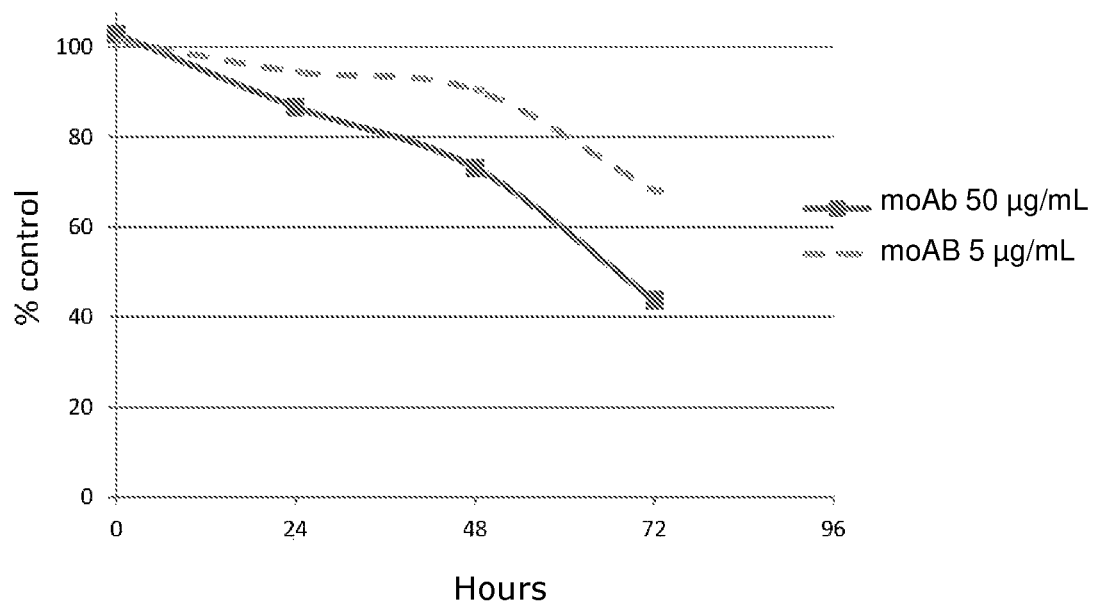
FIG. 3. Viability analysis of the tumor cell lines MCF7 in the presence of the moAb monoclonal antibody of the invention that specifically binds to SEQ ID NO: 1, to concentrations of 5 and 50 μg/ml, for 0, 24, 48 and 72 h, with respect to the control group not treated with said antibody. Cell growth was measured with the MTT assay and is expressed as a percentage with respect to the control cells.
Figure 4:
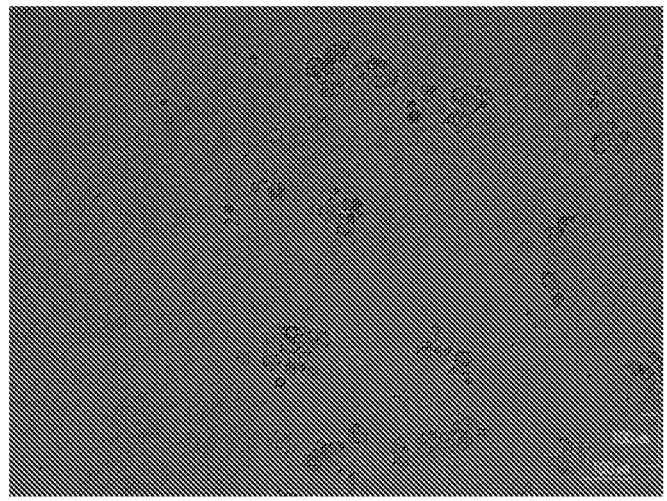
FIG. 4A. Images of MCF7 cell line in the presence of the moAb monoclonal antibody of the invention that specifically binds to SEQ ID NO: 1, to the concentrations of 5 μg/ml for 72 h.
FIG. 4B is an image of the control group not treated with said antibody as shown.
Figure 4:
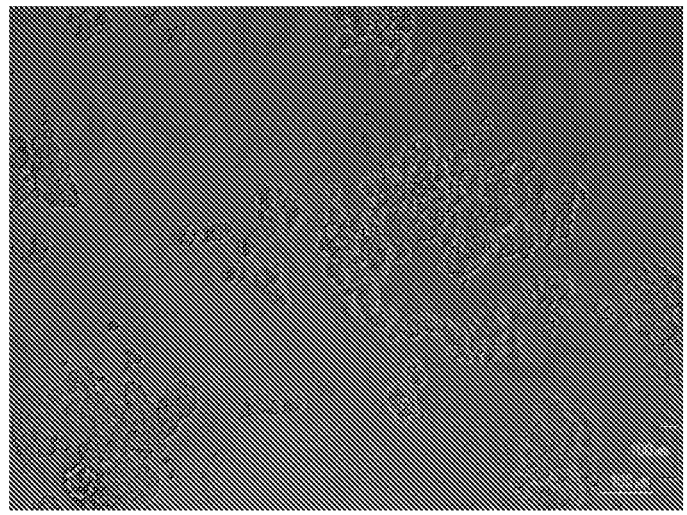

Additionally, FIG. 3 demonstrates that the treatment of MCF7 cells with the anti-presenilin 1 moAb of the invention, at concentrations of 5 μg/ml or 50 μg/ml, is capable of inhibiting the viability of said cell line tumor compared to control cells. Table 3 shows the viability percentages of the moAb of the invention at the doses tested and with respect to the control.

TABLE 3

Viability percentage of MCF7 cells treated with the moAB.

|  |  | moAb | |
| --- | --- | --- | --- |
| Time | Control | 50 μg/mL | 5 μg/mL |
| 0 | 100 | 102.9 | 101.51 |
| 24 | 100 | 86.68 | 94.55 |
| 48 | 100 | 73.13 | 90.50 |
| 72 | 100 | 43.75 | 68.02 |

The invention claimed is:

1. A pharmaceutical composition for treating cancer, comprising:
   a polyclonal antibody or fragment thereof that specifically binds to SEQ ID NO: 1; Apo2L (Trail); and
   a pharmaceutically acceptable carrier and/or excipient.

2. The pharmaceutical composition according to claim 1, wherein the cancer is selected from the group consisting of lung cancer, non-small cell lung cancer, small cell lung cancer, bone cancer, pancreatic cancer, skin cancer, head or neck cancer, cutaneous melanoma, uterine cancer, ovarian cancer, rectal cancer, gastric cancer, colon cancer, breast cancer, Fallopian tube carcinoma, endometrial carcinoma, cervical carcinoma, vaginal carcinoma, vulvar carcinoma, esophageal cancer, small intestine cancer, urethral cancer, prostate cancer, bladder cancer, kidney or ureter cancer, renal cell carcinoma, central and peripheral nervous system tumors, spinal cord tumors, brainstem glioma, glioblastoma multiforme, astrocytoma, medulloblastomas, meningiomas and squamous cell carcinoma.

3. The pharmaceutical composition according to claim 1, wherein the cancer is selected from the group consisting of breast cancer, head and neck cancer, colon cancer, prostate cancer and glioblastoma.

4. The pharmaceutical composition according to claim 1, wherein the polyclonal antibody or fragment thereof is from hen.

* * * * *